US00PP34556P2

(12) United States Plant Patent
Shoup

(10) Patent No.: US PP34,556 P2
(45) Date of Patent: Sep. 13, 2022

(54) SHRUB ROSE PLANT NAMED 'ALWAYS HOPE'

(50) Latin Name: *Rosa hybrida*
Varietal Denomination: Always Hope

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 0 days.

(21) Appl. No.: 17/484,895

(22) Filed: Sep. 24, 2021

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

*Primary Examiner* — Karen M Redden

(57) ABSTRACT

A new and distinct variety of shrub rose plant, herein referred to by its cultivar name, 'Always Hope', is provided which abundantly, substantially, and continuously forms exceptionally large displays of semi-double pink colored blooms. The growth habit is rounded and bushy. The foliage is smooth, and dark green with a slightly waxy finish. The plant propagates from cuttings easily, has a unique characteristic of consistently producing an exceptional amount of rose hips. The new variety is well suited for growing as a wildlife attractor, as a hedge, and as a source of attractive ornamentation in the landscape.

1 Drawing Sheet

Botanical/commercial classification: Latin name: *Rosa hybrida.*

Varietal denomination: 'Always Hope'.

SUMMARY OF THE INVENTION

The new variety of *Rosa hybrida* shrub rose plant was created at Brenham, Tex., U.S.A., by artificial pollination wherein two parents were crossed which previously had been observed in the hope that each would contribute their desired traits. The female parent (i.e., the seed parent) was the 'Radgor' variety (U.S. Plant Pat. No. 25,628). The male parent (i.e., the pollen parent) was the 'Gideon Lincecum' variety (non-patented in the United States). The parentage of the new variety can be summarized as follows:

'Radgor' x 'Gideon Lincecum'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new shrub rose plant of the present invention possesses the following combination of characteristics:

(a) abundantly, substantially, and continuously forms large displays of pink colored blooms,
(b) exhibits an exceptionally high bloom to foliage ratio when blossoming,
(c) exhibits a bushy and round growth habit,
(d) exhibits an exceptional amount of fruit (i.e., rose hip) production,
(e) forms disease resistant foliage with a smooth and glossy finish, and
(f) is well suited for growing as a wildlife attractor, a hedge, and as a source of attractive ornamentation in the landscape.

The new rose can be readily distinguished from its ancestors upon observing the bloom to foliage ratio when blossoming, that is total bloom coverage of the foliage, also called bloom power. More specifically, the 'Always Hope' variety forms approximately 50% more blooms when blossoming when compared to the dissimilar parental variety 'Radcor'. The new variety can also be readily distinguished from its ancestors upon observing the rose hip production. The new variety 'Always Hope' forms an exceptional amount of rose hips, while the parental variety 'Radcor' dissimilarly does not form rose hips unless manually pollinated with the pollen of another variety. The other parental variety, 'Gideon Lincecum' does produce rose hips, however they are smaller in size and less abundant than the 'Always Hope' variety.

The new variety of the present invention also can be readily distinguished from other shrub rose plants, including the 'Radcon' variety (U.S. Plant Pat. No. 15,070) upon inspection of the blossoms. For example, the 'Radcon' variety forms dissimilar thinner petalled blossoms when compared to 'Always Hope' which exhibits petals thicker and more durable in comparison.

Asexual reproduction of 'Always Hope' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Always Hope' remain stable, uniform and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, 'Always Hope'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V. The description is based one year old specimens of the new variety during August while growing outdoors on their own roots at Brenham, Tex., U.S.A.

Class: Landscape Shrub Rose. Cultivar 'Always Hope'.

Plant:

*Height.*—Approximately 0.7 m on average at maturity.

*Width.*—Approximately 0.9 m on average at maturity.

*Habit.*—Shrub-like, erect.

Stems:

*Size.*—Approximately 66 cm tall by 1.1 cm in caliper.

*Color.*—Immature: Turquoise-Green Group 144C. Mature: Turquoise-Green Group 144A.

*Prickles.*—Size: Approximately 1 cm in length on average. Quantity: Slightly below average when compared to other shrub roses. Color: Turquoise-Green Group N144A. Shape: Declining, intrastipular, very slightly setaceous. Density: Irregularly spaced throughout the stems.

*Texture.*—Smooth.

*Internodal spacing.*—Approximately 4.5 cm on average.

Leaves:

*Arrangement.*—Alternate, odd-pinnate, and compound.

*Margin.*—Serrate.

*Stipules.*—Size: Approximately 1.5 cm×1.1 cm on average. Margin: Adnate, and gland-laciniate. Color: Turquoise-Green Group 144A. Texture: Smooth.

*Size.*—Approximately 13 cm×9.5 cm on average.

*Petioles.*—Color upper surface: Turquoise-Green Group 141A. Color under surface: Turquoise-Green Group N144A. Size: Approximately 6 cm×0.9 mm on average. Shape: Filiform.

*Rachis.*—Color: Turquoise-Green Group N144A.

*Leaflets.*—Number: 5 and 7. Shape: Ovate-lanceolate. Size: Approximately 4 cm×2.25 cm on average. Venation: Reticulate. Venation Color: Turquoise-Green Group 141A. Apex: Acute. Base: Cuneate. Texture Upper Surface: Smooth, slightly waxy. Texture Under Surface: Matte. Overall Appearance: Very dark green. Color (Young Foliage) Upper Surface: Turquoise-Green Group 144C. Color (Young Foliage) Under Surface: Turquoise-Green Group 144C. Color (Adult Foliage) Upper Surface: Turquoise-Green Group 141A. Color (Adult Foliage) Under Surface: Turquoise-Green Group 144D.

Inflorescence:

*Average size of inflorescence.*—Approximately 16 cm×13 cm on average.

*Number of flowers per inflorescence.*—Approximately 17 on average.

*Florescence type.*—Paniculate.

*Peduncle.*—Color: Turquoise-Green Group 144A. Length: Approximately 4.25 cm on average. Diameter: Approximately 1.75 mm on average. Texture: Gland-ciliate.

*Sepals.*—Number: 5. Size: Approximately 2.6 cm×0.7 mm on average. Arrangement: Pentamerous and imbricate. Shape: Obcuneate. Margin: Laciniate. Apex: Acute, appendiculate. Base: Obtuse. Texture: Gland-ciliate. Color Upper Surface: Turquoise-Green Group 143B. Color Under Surface: Turquoise-Green Group 143B.

*Buds.*—Shape: Ovoid. Size: Approximately 2 cm to 1.25 cm on average. Color (When Opening) Inner Surface: Purple-Blue Group 63A. Color (When Opening) Outer Surface: Purple-Blue Group 58B.

Flower:

*Form.*—Semi-double.

*Diameter.*—Approximately 7.5 cm on average.

*Color.*—(When Opening) Upper Surface: Purple-Blue Group 63A. (When Opening) Under Surface: Purple-Blue Group 58B. (When Blooming) Upper Surface: Purple-Blue Group 58C. (When Blooming) Under Surface: Purple-Blue Group 58D. (End Of Blooming) Upper Surface: Purple-Blue Group 62D. (End Of Blooming) Under Surface: Purple-Blue Group 62D.

*Fragrance.*—Nondetectable.

*Petal form.*—Obchordate.

*Petals.*—Size: Approximately 3 cm×2.7 cm on average. Margins: Entire. Apex: Chordate. Base: Acute. Texture: Smooth. Number: Approximately 8 on average. Petaloids: None present. Petal Drop: Subfugacious.

*Stamen number.*—Approximately 125 on average.

*Anther color.*—Yellow-Red Group 14A.

*Anther shape.*—Oblong.

*Anther length.*—Approximately 2 mm on average.

*Filament color.*—Yellow-Red Group 14B.

*Filament length.*—Approximately 6 mm on average.

*Pollen quantity.*—Profuse.

*Pollen color.*—Yellow-Red Group 17A.

*Pistil form.*—Villous and free.

*Pistil number.*—Approximately 34 on average.

*Stigma color.*—Yellow-Red Group 7D.

*Style color.*—Yellow-Red Group 4D.

*Style length.*—Approximately 4 mm on average.

*Receptacle.*—Rhomboidal to globose. Achenes form on the inside of the fruit. Size: Approximately 0.6 cm×0.7 cm on average when mature.

*Rate of flower opening.*—Fast.

*Lasting quality.*—On plant: Approximately 2 to 3 days on average. In vase: Unknown.

Development:

*Vegetation.*—Vigorous and leathery.

*Growth rate.*—Average.

*Hip/seed formation.*—Profuse and abundant.

Root system:

*Root color.*—Yellow-Red Group 20D.

*Root habit.*—Well rounded.

Physiology:

*Disease resistance.*—Above average resistance to black spot *Diplocarpon rosae,* downy mildew *Peronospora sparsa*, powdery mildew *Podosphaera pannosa*, and cercospora leaf spot *Cercospora rosicola.*

*Cold hardiness.*—The variety has been found to be suitable for climactic conditions in USDA Plant Hardiness Zone 8. Based on the performance of its parent varieties, it is likely, although untested, that the new variety is suitable for climatic conditions of USDA Plant Hardiness Zones 6 and 7.

*Heat tolerance.*—The new variety exhibits no unique heat tolerance. The variety has been found to be suitable for climactic conditions in USDA Plant Hardiness Zone 8.

*Drought tolerance.*—The new variety exhibits average drought tolerance.

I claim:

1. A new and distinct variety of shrub rose plant named 'Always Hope' characterized by the following combination of characteristics:

(a) abundantly, substantially, and continuously forms large displays of pink colored blooms, (b) exhibits an exceptionally high bloom to foliage ratio when blossoming, (c) exhibits a bushy and round growth habit, (d) exhibits an exceptional amount of fruit (i.e., rose hip) production, (e) forms disease resistant foliage with a smooth and glossy finish, and (f) is well suited for growing as a wildlife attractor, a hedge, and as a source of attractive ornamentation in the landscape.

substantially as illustrated and described herein.

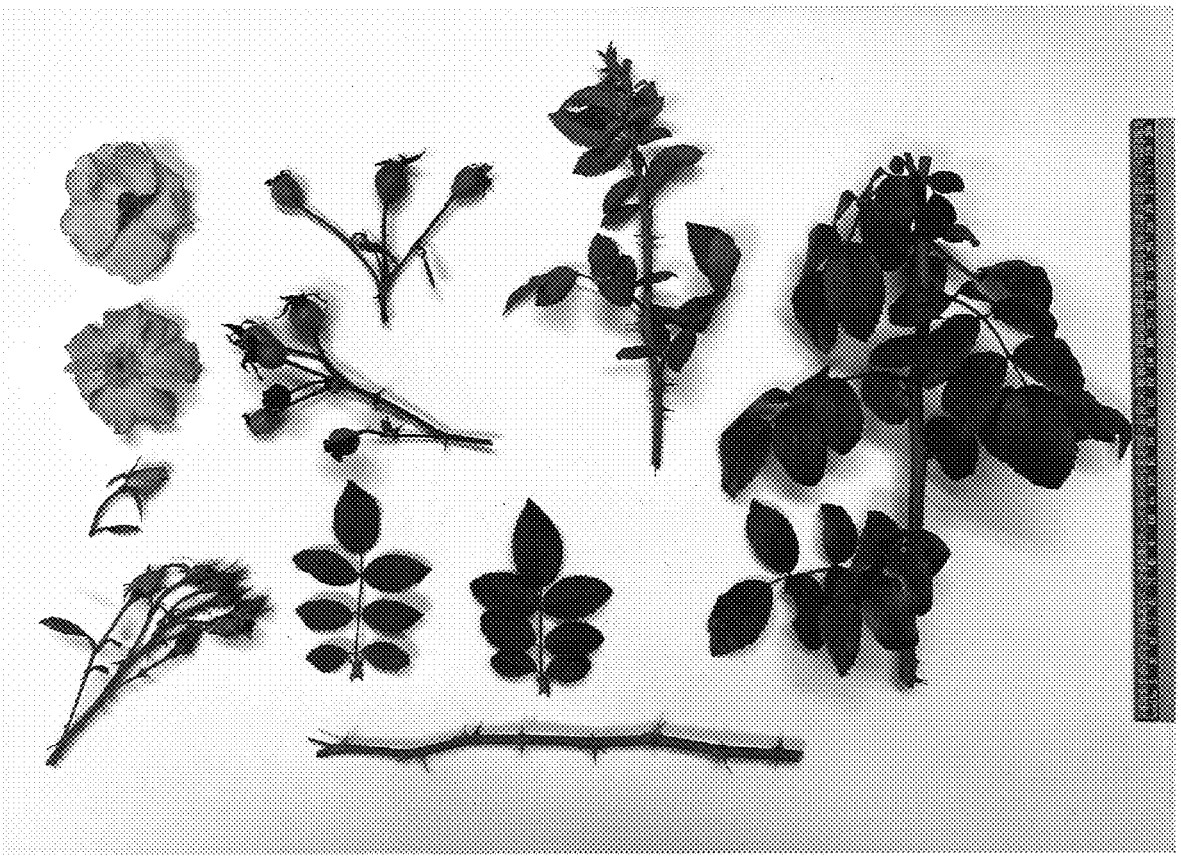

* * * * *